United States Patent [19]
Huebner et al.

[11] Patent Number: 6,017,347
[45] Date of Patent: Jan. 25, 2000

[54] WIRE CLAMP ASSEMBLY

[75] Inventors: Randall J. Huebner, Beaverton; Steven P. Horst, Dayton, both of Oreg.

[73] Assignee: Acumed, Inc., Beaverton, Oreg.

[21] Appl. No.: 09/305,841

[22] Filed: May 5, 1999

Related U.S. Application Data

[63] Continuation-in-part of application No. 09/157,783, Sep. 21, 1998, which is a continuation-in-part of application No. 08/457,624, Jun. 1, 1995, Pat. No. 5,810,825.

[51] Int. Cl.⁷ .................................................. A61B 17/56
[52] U.S. Cl. ................ 606/74; 606/69; 606/103
[58] Field of Search .................. 606/69, 70, 71, 606/72, 74, 75, 103

[56] References Cited

U.S. PATENT DOCUMENTS

| | | |
|---|---|---|
| 76,141 | 3/1868 | Barnum . |
| 190,641 | 5/1877 | Stouffer . |
| 866,144 | 9/1907 | Kobert . |
| 2,171,524 | 9/1939 | Gates . |
| 2,276,571 | 3/1942 | Grypman . |
| 2,464,432 | 3/1949 | Brickman . |
| 2,986,787 | 1/1961 | Ackermann . |
| 3,641,629 | 2/1972 | Beardsley . |
| 3,754,303 | 8/1973 | Pollock . |
| 4,269,180 | 5/1981 | Dall et al. . |
| 4,473,925 | 10/1984 | Jansen . |
| 4,527,308 | 7/1985 | Tritton et al. . |
| 4,643,178 | 2/1987 | Nastari et al. . |
| 4,688,560 | 8/1987 | Schultz . |
| 4,790,303 | 12/1988 | Steffee . |
| 4,889,110 | 12/1989 | Galline et al. ............................. 606/69 |
| 4,896,668 | 1/1990 | Popoff et al. . |
| 5,051,543 | 9/1991 | McGuire . |
| 5,190,545 | 3/1993 | Corsi et al. . |
| 5,312,410 | 5/1994 | Miller et al. . |
| 5,318,566 | 6/1994 | Miller . |
| 5,356,412 | 10/1994 | Golds et al. . |
| 5,415,658 | 5/1995 | Kilpela et al. ............................. 606/57 |
| 5,476,465 | 12/1995 | Preissman . |
| 5,649,927 | 7/1997 | Kilpela et al. . |
| 5,693,046 | 12/1997 | Songer et al. . |
| 5,702,399 | 12/1997 | Kilpela et al. . |
| 5,741,260 | 4/1998 | Songer et al. . |

*Primary Examiner*—Michael Buiz
*Assistant Examiner*—Daphna Shai
*Attorney, Agent, or Firm*—Kolisch Hartwell Dickinson McCormack & Heuser

[57] ABSTRACT

A wire locking sleeve and a wire. The sleeve has a bore and a deformation recess adjacent the bore. The sleeve includes a locking stud positioned adjacent the deformation recess and bore. The locking stud is deformable toward the bore interlockingly to engage a portion of the wire disposed therein. Deformation of the sleeve around the bore is achieved by applying a transverse compressive force to the locking stud.

20 Claims, 5 Drawing Sheets

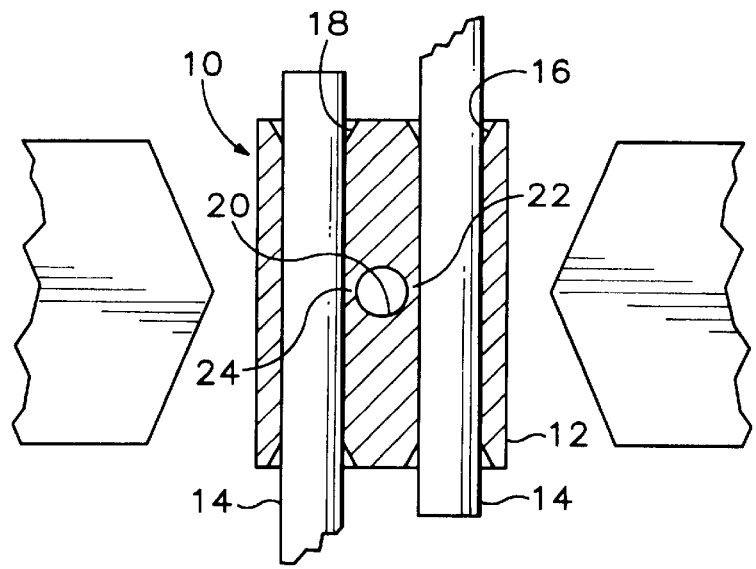
FIG.6
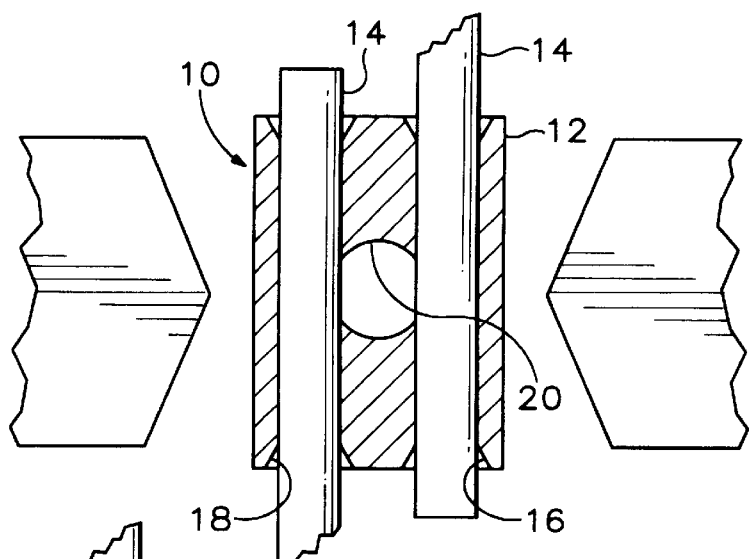
FIG.7
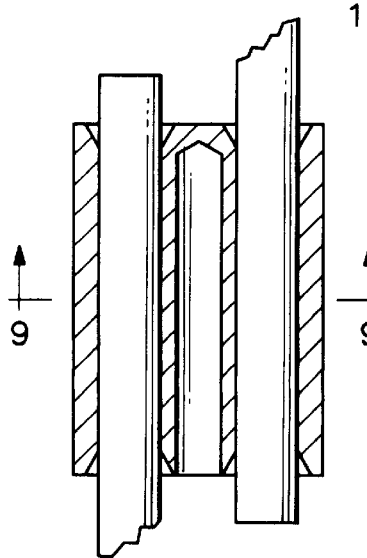
FIG.8
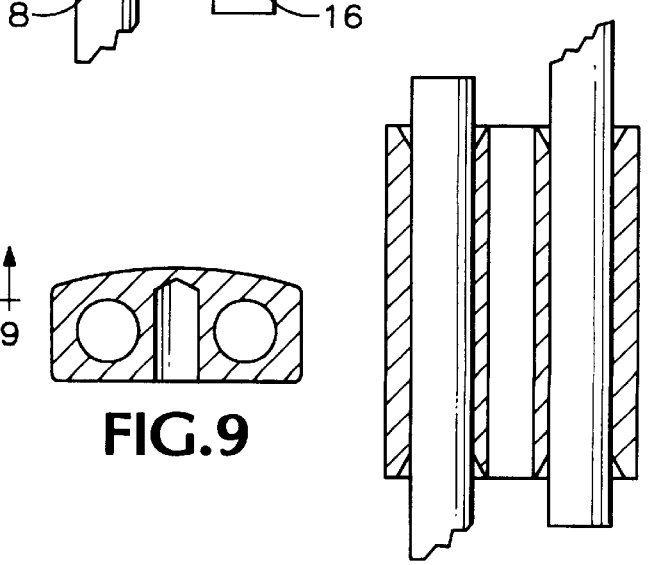
FIG.9
FIG.10

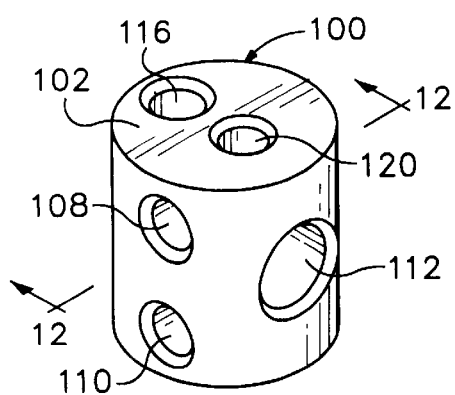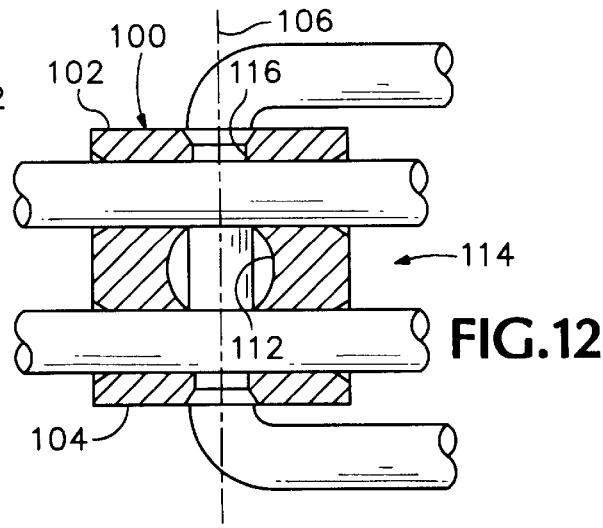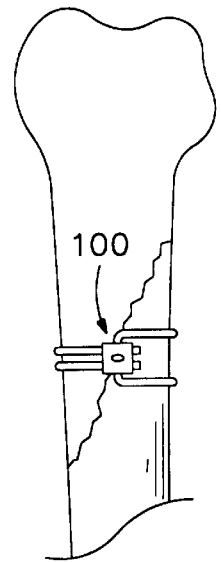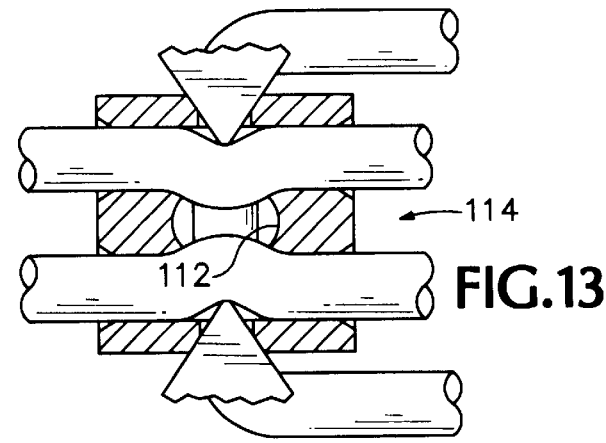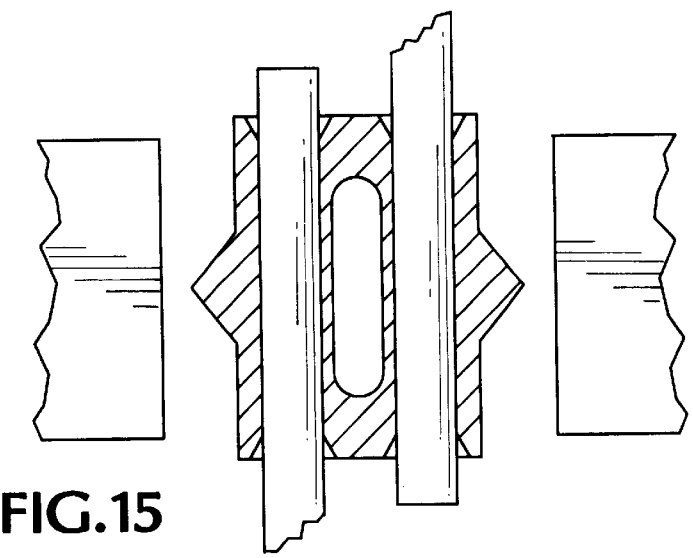
FIG.11
FIG.12
FIG.13
FIG.14
FIG.15

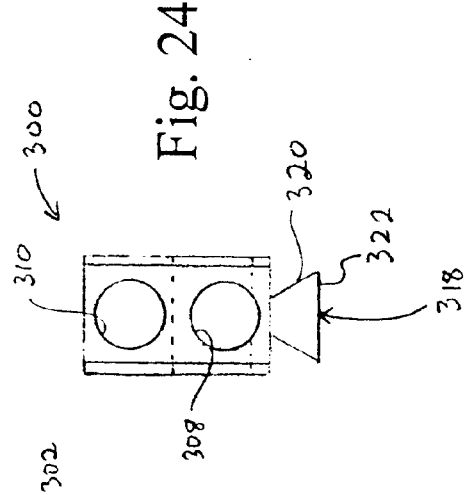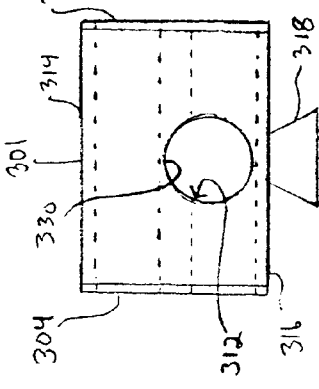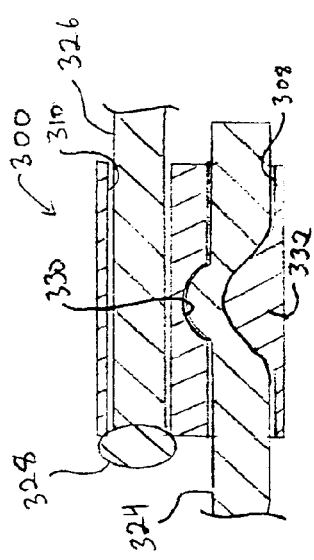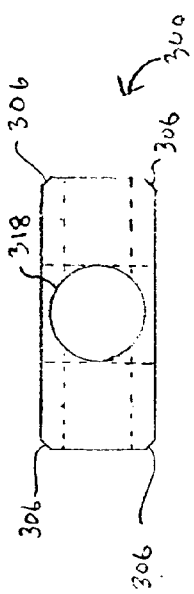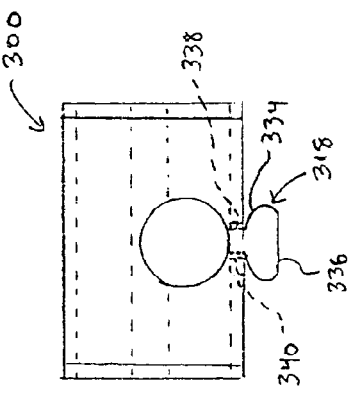

WIRE CLAMP ASSEMBLY

CROSS-REFERENCE TO RELATED APPLICATION

This application is a continuation-in-part of U.S. patent application Ser. No. 09/157,783, filed Sep. 21, 1998, which is a continuation-in-part of U.S. patent application Ser. No. 08/457,624, filed Jun. 1, 1995, issued as U.S. Pat. No. 5,810,825, on Sep.22, 1998.

BACKGROUND OF THE INVENTION

The present invention relates to wire clamp assemblies and in particular, to a wire and sleeve assembly for securing together portions of a fractured bone to facilitate healing.

It is routine surgical practice to bind portions of a fractured bone together to ensure their proper alignment and to facilitate the knitting together of the bone portions. Wire and clamp assemblies are typically used for this purpose. Such assemblies can be subjected to very high tensile forces when, for example, the fractured bone is subjected to a high bending moment.

It is therefore important that the wire and clamp assembly embody the highest possible resistance to tensile forces which may cause such failures.

Known wire and clamp assemblies, as exemplified in FIG. 1, include a stranded, stainless steel cable and a sleeve having a pair of bores to receive the ends of the cable. Each cable end is clamped in one bore by urging the outer wall of the bore against the cable, squeezing the cable between the outer wall of the bore and the solid central portion of the sleeve. While such wire and clamp assemblies perform satisfactorily in most cases, they sometimes fail under high bending forces exerted on the fractured bone as described above. Moreover, the stranded stainless steel wire used in such assemblies is relatively expensive. A need therefore remains for a stronger, less expensive wire and clamp assembly for binding fractured bones.

SUMMARY OF THE INVENTION

The wire clamp of the present invention comprises a wire locking sleeve and a wire. The sleeve has a bore and a deformation recess adjacent the bore. The sleeve around the bore is deformable toward the recess into a serpentine configuration for interlockingly engaging a portion of the wire disposed therein. Deformation of the sleeve around the bore is achieved by applying a transverse compressive force to the sleeve.

The invention is also embodied in a method of securing a wire including the steps of providing a crimp block, the crimp block having a first wire-receiving bore formed therein and a deformation recess formed proximal to a region of the wire-receiving bore, the first wire-receiving bore being slightly larger than the wire, inserting a portion of the wire into the wire-receiving bore and deforming a section of the wire proximal to the deformation recess, and the portion of the crimp block surrounding the section of the wire, toward the deformation recess to form a concavity in the wire and the wire-receiving bore.

BRIEF DESCRIPTION OF THE DRAWINGS

FIG. 6 is a cutaway plan view of an alternative embodiment of the wire clamp assembly having a circular opening.

FIG. 7 is a cutaway plan view of an alternative embodiment of the wire clamp assembly where the circular opening communicates with the longitudinal bores.

FIG. 8 is a cross-sectional view of an alternative embodiment of a sleeve according to the present invention.

FIG. 9 is a cross-sectional end view of the sleeve of FIG. 8, taken along line 9—9.

FIG. 10 is a cross-sectional view of an alternative embodiment of a sleeve according to the present invention.

FIG. 11 is a perspective view of an alternative embodiment of a sleeve according to the present invention.

FIG. 12 is a cross-sectional view of the sleeve of FIG. 11, taken along line 12—12.

FIG. 13 is a cross-sectional view of the sleeve of FIG. 11, taken along line 12—12, after deformation.

FIG. 14 shows the sleeve of FIG. 11 applied to repair a bone.

FIG. 15 is a cross-sectional view of an alternative embodiment of a sleeve according to the present invention.

FIG. 22 is a top view of another embodiment of a sleeve according to the present invention.

FIG. 23 is a front view of the sleeve of FIG. 22.

FIG. 24 is a side view of the sleeve of FIG. 22.

FIG. 25 is a cross-sectional view of the sleeve of FIG. 22 with a wire secured therein.

FIG. 26 is a top view of another embodiment of a sleeve according to the present invention.

DETAILED DESCRIPTION

Figure 1:
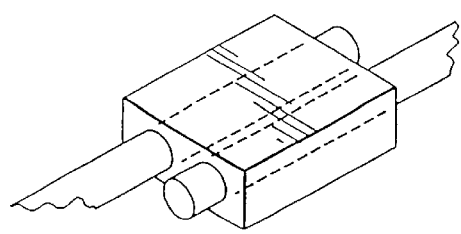
FIG. 1 is a perspective view of a prior art wire clamp assembly.
Figure 2:
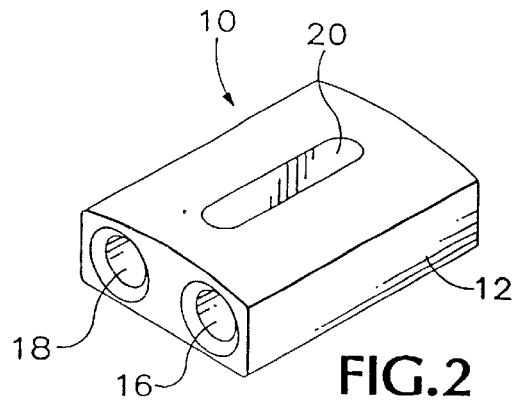
FIG. 2 is perspective view of one embodiment of a wire clamp sleeve according to the present invention.

Referring now to FIGS. 2–7, a wire clamp 10 according to the present invention includes a body 12 and a wire 14. Body 12, also referred to as securing member 12, includes longitudinal bores 16 and 18, which preferably extend through the body. In alternative embodiments, either or both of longitudinal bores 16 and 18 may be blind bores which do not extend through body 12 and may be a blind hole, as shown in FIG. 8, or a blind channel, as shown in FIG. 9, or may be a thru-hole extending completely through to opposing sides of body 12, as shown in FIG. 10. A vertical opening 20, also referred to as deformation recess 20, extends through body 12 and is preferably located between longitudinal bores 16 and 18, and is round, as shown in FIGS. 6 and 7. In alternative embodiments, opening 20 may be shaped differently, including but not limited to the oblong shape shown in FIG. 3. Opening 20 may extend only partially through body 12. In the embodiments shown in FIGS. 2–6, vertical opening 20 and longitudinal bores 16 and 18 together define walls 22 and 24, respectively. Wire 14 is a surgical grade wire, typically made of stainless steel. In the preferred embodiment, wire 14 is monofilament for reasons described below, but may also be stranded.

Figure 3:
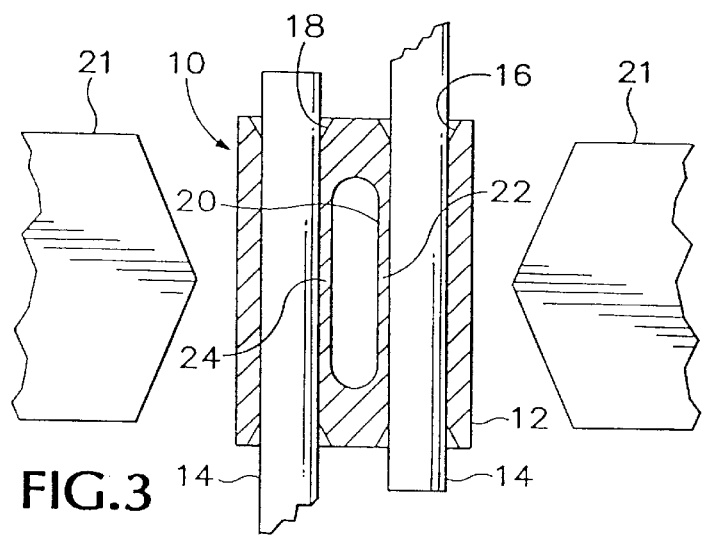
FIG. 3 is a cutaway plan view of the wire clamp of FIG. 2 having first and second ends of the wire inserted into the respective first and second longitudinal bores.
Figure 4:
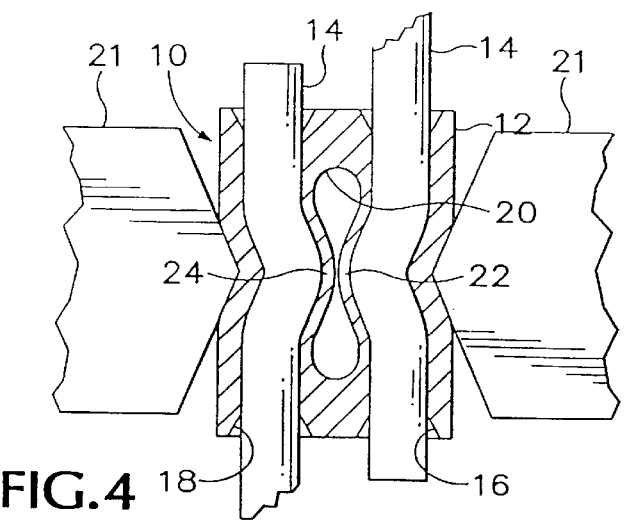
FIG. 4 is a cutaway plan view of the wire and clamp assembly shown in FIG. 3 wherein the longitudinal bores, longitudinal walls, and the wire ends have been deformed into interlocking serpentine configurations.
Figure 5:
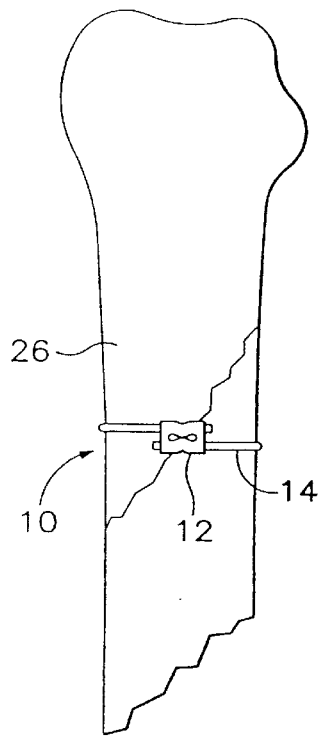
FIG. 5 is a top view of a wire and clamp assembly according to the present invention which has been applied to stabilize a fractured bone.
Figure 16:
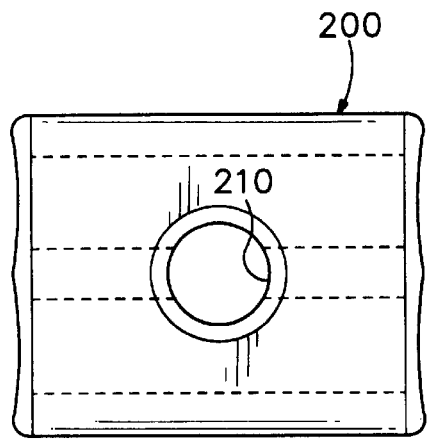
FIG. 16 is a top view of an alternative embodiment of a sleeve according to the present invention.
Figure 17:
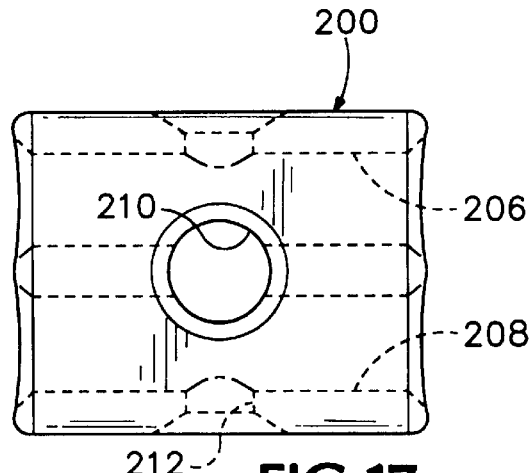
FIG. 17 is a bottom view of the sleeve of FIG. 16.
Figure 18:
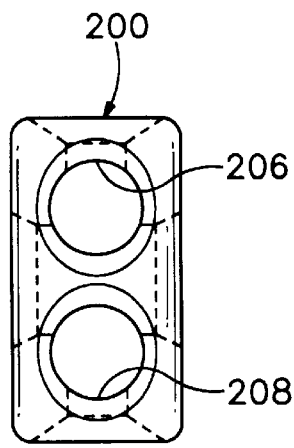
FIG. 18 is an end view of the sleeve of FIG. 16.
Figure 19:
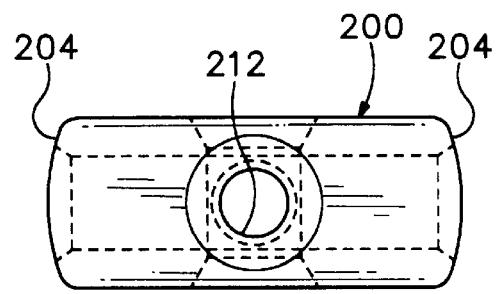
FIG. 19 is a side view of the sleeve of FIG. 16.

Wire clamp 10 is applied by passing wire 14 around fractured bone 26 in FIG. 5, inserting the wire ends into longitudinal bores 16 and 18, and then drawing them tight (FIGS. 3, 5). Pliers 21, also referred to as crimping tool 21, with pointed jaws, are then squeezed against body 12 to deform longitudinal bores 16 and 18 and the wire ends into interlocking, serpentine configurations (FIG. 4). FIG. 15 illustrates a variation of the sleeve of FIG. 3 in which ridges or bumps 30 are formed on the surface of the sleeve. This allows the sleeve to be deformed using a flat jawed tool or with a hammer. Deformation of the body surrounding the longitudinal bores into a serpentine bore configuration is facilitated by opening 20, which allows deformation of walls 22 and 24. The serpentine bore configuration achieved with the present invention provides greater clamping force than has heretofore been possible with prior art clamps in which only the outer wall of each longitudinal bore is urged against the stranded wire, but in which the inner wall of the bore is not deformable by any level of compressive forces that can be readily applied in a surgical setting. Although the embodiments of the present invention are described in the context of a surgical application, it should be understood that the wire clamp of the present invention can be used wherever wire or cables must be secured. In addition, the crimp block could be formed as part of another object to allow anchoring of wires or cables, such as in an electrical terminal block.

Applicant has discovered that use of a monofilament, stainless steel surgical wire in conjunction with the serpentine configuration increases the strength of the wire clamp assembly even further. Increased strength is achieved by using a monofilament wire for at least two reasons. First, the stainless steel monofilament wire undergoes plastic deformation as it is deformed into its serpentine configuration. If the deformed monofilament wire is to be pulled from the body, sufficient force must be applied to rework the wire as it passes through the serpentine bore. Reworking the wire is particularly difficult because the wire was work-hardened during its initial deformation. Also, there are three separate bends that must be reworked to slide the wire. Stranded wire, on the other hand, is more resilient, and does not plastically deform or work-harden as much as monofilament wire when urged into the serpentine configuration achieved in the present invention. As a result, stranded wire can be separated from the body by a lesser force than that required for monofilament wire. Moreover, this greater strength achieved by use of monofilament wire is achieved at lower overall cost compared to stranded stainless steel wire.

Figure 21:
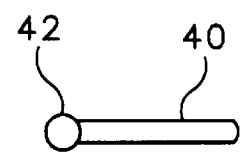
FIG. 21 shows a portion of a wire adapted for use in the present invention.

In an alternative embodiment (not shown), the clamp comprises a body 12 and a wire 14 having a first end permanently fixed in bore 16, and a second distal end. Body 12 has a longitudinal bore 18 to receive the distal end of wire 14. In use, the distal end of wire 14 is passed around the fractured bone and inserted into bore 18. Bore 18 and the second wire end are then deformed into an interlocking, serpentine configuration by use of a plier, as described above. This embodiment provides the advantage of having only one portion of the wire which is slidable relative to the body, rendering installation easier in some instances. Alternatively, as shown in FIG. 21, a wire 40 with a beaded end 42 can be used to accomplish the same result. The bead catches on the end of the sleeve and prevents the wire from sliding out of the sleeve.

Another embodiment of the present invention is shown in FIGS. 11–14. As shown in FIG. 11, the wire locking system of this embodiment includes a crimp sleeve 100. Crimp sleeve 100 is generally cylindrical with first and second ends 102, 104 extending transverse to a cylindrical axis 106. First and second wire-receiving bores 108, 110 extend through the sleeve in a direction transverse to the cylindrical axis. A deformation recess 112 extends through the sleeve in a direction transverse to the cylindrical axis, as well as the axis of bores 108, 110. Recess 112 extends between the bores in a crimp zone 114 to provide room for the required locking deformation to occur. A crimp hole 116 is formed parallel to cylindrical axis 106, bisecting bores 108, 110. The crimp hole allows pointed tips 118 of a crimping tool (not shown) to apply force directly to the sections of wire disposed in bores 108, 110, as shown in FIG. 13. A third wire-receiving bore 120 is formed parallel to cylindrical axis 106 to receive a central portion of the wire therethrough, as shown in FIG. 14. In this configuration, the ends of the wire are received in bores 108, 110 to form a double-wire securing structure. While the various described embodiments involve securing the ends of a wire to form a loop, the invention can also be implemented with only one wire-receiving bore, as where only one end of a wire is to be anchored. In such cases the sleeve would typically be formed as part of, or attached to, some other structure.

Figure 20:
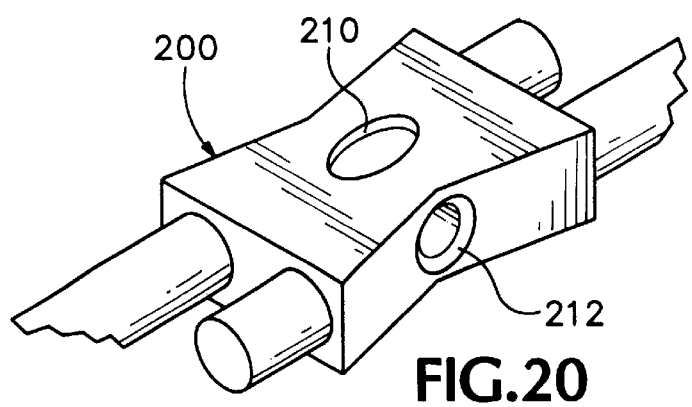
FIG. 20 is an isometric view of the sleeve of FIG. 16.

FIGS. 16–20 show a wire locking sleeve 200 according to one embodiment of the present invention. Sleeve 200 includes curved ends 202, 204 and first and second parallel, spaced-apart wire-receiving bores 206, 208 extending therebetween. A deformation recess 210 extends through the sleeve transverse to and between the wire-receiving bores. A crimp hole 212 transversely bisects the wire-receiving bores and the deformation recess to provide access for a crimping tool, as described above. When pressure is applied to the sides of the sleeve at the crimp hole ends, the sleeve is deformed inwardly toward the deformation recess, as shown in FIG. 20. Sleeve 200 is preferably formed from quarter-inch diameter round biocompatible stock, typically stainless steel or titanium. By virtue of the design and position of the holes, it is possible to manufacture the sleeve using only a screw machine.

One advantage of certain embodiments of the present invention is that they do not rely on deformation of the wire to achieve grip. This allows use of much harder wire, such as stainless steel or titanium, than can be used with sleeves that rely on deforming the cross-section of the wire to grip, as is the case with many sleeves designed for use with copper wire.

FIGS. 22–25 show a wire locking crimp block 300 according to another embodiment of the present invention. Crimp block 300 typically includes a body 301 with opposed first and second ends 302, 304, including chamfered regions 306. Crimp block 300 includes first and second parallel, spaced-apart wire-receiving bores 308, 310 extending between first and second ends 302, 304. A deformation recess or cavity 312 extends through crimp block 300, the deformation recess being oriented transverse to each of first and second wire-receiving bores 308, 310 and positioned such that deformation recess 312 intersects the first bore.

Deformation recess 312 also typically includes a region of nonintersection 330, located outside of and immediately adjacent the first bore. The deformation recess typically extends from a top to a bottom of the crimp block. Alternatively, the deformation recess may extend into the crimp block from a rear side 314 toward a front side 316 of the crimp block.

Crimp block or securing member 300 includes a bump in the form of a locking stud 318 positioned on front side 316, adjacent deformation recess 312. Locking stud 318 typically is frustoconical in shape, and includes a base 322 and a tapered side 320. The tapered side typically narrows toward deformation recess 312 and first wire-receiving bore 308. Base 322 is configured to receive force from a crimping tool, such as a pair of pliers, such that locking stud 318 may be crimped and deformed into deformation recess 312 and first bore 308. It should be noted that, although the crimp block, as depicted in FIGS. 22–25, includes only one locking stud, a stud could be provided for each bore so that both wires are locked in place. In addition, there are some applications where only one wire is used so that the crimp block may be formed with a single wire-receiving bore.

As shown in FIG. 26, locking stud 318 may alternatively include a flat end 336 and curved sides that include a tapered region 334 that generally narrows toward the first wire-receiving bore and deformation recess. It will be understood by those of ordinary skill in the art that many shapes are possible for the locking stud. For example, locking stud 318 may be wedge-shaped, spherical, or some other irregular shape including a reduced cross-section toward the first bore.

Typically, locking stud 318 is formed integrally with crimp block 300, as shown in FIG. 22. Alternatively, the locking stud may be structurally independent, and include a shaft 338 positioned within a hole 340 in the crimp block, as shown in FIG. 26. For example, the locking stud may be interference fit or press fit within hole 340.

In FIG. 25, crimp block 300 is shown in a crimped configuration in which a wire is secured within the crimp block. The wire typically includes a first section 324 and a second section 326 with a cap 328. Cap 328 is wider than the second wire-receiving bore. The second section of the wire is positioned in the second wire-receiving bore such that cap 328 rests securely against an end of the crimp block. The first section of the wire is positioned in the first wire-receiving bore.

To secure the wire within the crimping block, a crimping tool is used to apply compressive force to deform locking stud 318 into deformation recess 312 and first wire-receiving bore 308, thereby also deforming the first portion of wire. As with the embodiment of FIG. 15, it is also possible to compress the locking stud with a hammer or other impact-type tool in some applications. The first portion of wire is deformed partially out of first wire-receiving bore 308, into the region of nonintersection 330 of deformation recess 312 not contained within wire-receiving bore 308, thereby forming a generally serpentine, C-shaped bend in the first section of wire. In the crimped configuration, material from locking stud 318 forms a bulge 332 extending into the deformation recess 312 and first wire-receiving bore 308. Bulge 332 prevents first section 324 of wire from unwinding from its C-shaped bend, thereby securing the wire within the crimp block.

While the invention has been disclosed in its preferred form, the specific embodiments thereof as disclosed and illustrated herein are not to be considered in a limiting sense because numerous variations are possible. Applicants regard the subject matter of their invention to include all novel and non-obvious combinations and subcombinations of the various elements, features, functions, and/or properties disclosed herein. No single feature, function, element, or property of the disclosed embodiments is essential. The following claims define certain combinations and subcombinations which are regarded as novel and non-obvious. Other combinations and subcombinations of features, functions, elements, and/or properties may be claimed through amendment of the present claims or presentation of new claims in this or a related application. Such claims, whether they are broader, narrower, or equal in scope to the original claims, also are regarded as included within the subject matter of applicant's invention.

We claim:

1. A crimp block for securing a wire, the crimp block comprising:

a body including an outer surface;

a first wire-receiving bore formed in the body, the first wire-receiving bore being configured to receive a section of the wire; and a locking stud projecting from the outer surface of the crimp block proximate the first wire-receiving bore, the locking stud being smaller toward the first wire-receiving bore and larger away from the first wire-receiving bore;

where, upon application of a crimping force to the locking stud, the locking stud is configured to move toward the first wire-receiving bore thereby crimping the wire in the first wire-receiving bore.

2. The crimp block of claim 1, where the wire is configured to deform within the first wire-receiving bore upon movement of the locking stud toward the first wire-receiving bore.

3. The crimp block of claim 1, where the crimp block further includes a deformation recess adjacent the first wire-receiving bore opposite the locking stud, and the wire is configured to deform into the deformation recess upon movement of the locking stud toward the first wire-receiving bore.

4. The crimp block of claim 1, where the locking stud is substantially frustoconical.

5. The crimp block of claim 1, further comprising a deformation recess partially intersecting the first wire-receiving bore, the deformation recess including a region of nonintersection with the first wire-receiving bore, where movement of the locking stud toward the first wire-receiving bore deforms the wire at least partially into the region of nonintersection.

6. The crimp block of claim 5, where the locking stud is configured to form a bulge extending into the first wire-receiving bore as the locking stud is moved toward the first wire-receiving bore.

7. The crimp block of claim 1, wherein the locking stud is formed integrally with the crimp block.

8. The crimp block of claim 1, wherein the locking stud is a separate member.

9. A method of securing a wire, comprising:

providing a crimp block, the crimp block including a first wire-receiving bore, a deformation recess partially intersecting the first wire-receiving bore, the deformation recess including a region of nonintersection with the first wire-receiving bore, and a locking stud positioned proximate each of the deformation recess and first wire-receiving bore;

inserting a first section of the wire into the first wire-receiving bore; and deforming the shape of the locking stud into a bulge in the first wire-receiving bore, thereby deforming the first section of the wire into the region of nonintersection to secure the wire within the crimp block.

10. The method of claim 9, where deforming the locking stud includes forming a bulge within the first wire-receiving bore.

11. The method of claim 9, where the crimp block further includes an end and a second wire-receiving bore, and the wire further includes a second section having a cap wider than the second wire-receiving bore, the method further comprising inserting the second section of wire into the second wire-receiving bore such that the cap is adjacent the end of the crimp block.

12. The method of claim 9, where the wire is monofilament.

13. The method of claim 9, wherein the step of deforming is accomplished by squeezing a crimping tool against the locking stud.

14. The method of claim 9, where the locking stud tapers toward the deformation recess.

15. The method of claim 14, where the locking stud is substantially frustoconical.

16. A system for securing a wire comprising a crimp block having a monolithic body, the monolithic body including a first bore formed therein with a section of the wire being disposed in the first bore, the monolithic body further having a deformation recess disposed proximal to the first bore in a crimp zone, the wire and a portion of the monolithic body adjacent the first bore being locally deformed transverse to a first elongate axis of the wire in a sinuous shape around a bulge in the first bore toward the deformation recess in the crimp zone to interlock the wire in the first bore.

17. The system of claim 16, where the bulge is formed by deformation of a locking stud on the crimp block toward the deformation recess.

18. A system for securing a wire comprising a crimp block having a first bore formed therein with a section of the wire being disposed in the first bore, the crimp block further having a deformation recess disposed proximal to the first bore in a crimp zone, the wire and first bore being locally deformed transverse to a first elongate axis of the wire in a sinuous shape around a bulge in the first bore toward the deformation recess in the crimp zone to interlock the wire in the first bore, where the bulge is formed by deformation of a locking stud on the crimp block toward the deformation recess, and where the locking stud includes a taper that narrows towards the deformation recess.

19. The system of claim 18, where the locking stud is substantially frustoconical.

20. A crimp block for securing a wire, the crimp block comprising:
   a body including a generally straight crimp surface;
   a first wire-receiving bore formed in the body, the first wire-receiving bore being configured to receive a section of the wire and extending generally parallel to the crimp surface; and
   a locking stud projecting from the generally straight crimp surface of the crimp block, the locking stud being positioned to deform the crimp block into the first wire-receiving bore upon application of a crimping force to the locking stud.

* * * * *